United States Patent
Ahimou et al.

(10) Patent No.: US 11,065,355 B2
(45) Date of Patent: Jul. 20, 2021

(54) DEVICE FOR MONITORING EFFICACY OF A DECONTAMINATION PROCESS COMPRISING A BACTERIA CELL AND METHOD OF USING

(71) Applicant: 3M INNOVATIVE PROPERTIES COMPANY, Saint Paul, MN (US)

(72) Inventors: Francois Ahimou, Woodbury, MN (US); Assumpta A. G. Bennaars-Eiden, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 84 days.

(21) Appl. No.: 16/220,395

(22) Filed: Dec. 14, 2018

(65) Prior Publication Data
US 2019/0192714 A1    Jun. 27, 2019

Related U.S. Application Data

(60) Provisional application No. 62/609,624, filed on Dec. 22, 2017.

(51) Int. Cl.
*A61L 2/28*    (2006.01)
*A61B 90/70*    (2016.01)

(52) U.S. Cl.
CPC ................ *A61L 2/28* (2013.01); *A61B 90/70* (2016.02); *A61B 2090/702* (2016.02)

(58) Field of Classification Search
CPC .............................................. A61B 2090/702
See application file for complete search history.

(56) References Cited

FOREIGN PATENT DOCUMENTS

| WO | WO 2016-164329 | 10/2016 |
| WO | WO 2018-071618 | 4/2018 |
| WO | WO 2018-125798 | 7/2018 |

OTHER PUBLICATIONS

Schulze-Röbbecke et al., Tubercle and Lung Disease, 1992, 73:3141-144.*
Tasler et al., Vet Pathol., 1981, 18(1): 122-125.*
Goldman et al., American Review of Tuberculosis and Pulmonary Diseases, 1955, 73(5):674-680.*
Ko et al., J of the American Biological Safety Association, 1998, 3(2):65-78.*
Crowe, Science, 1984, 223:701-703.*
Centers for Disease Control and Prevention. 2008. *Infection Control*. 3 pages. Downloaded from https://www.cdc.gov/infectioncontrol/guidelines/disinfection/rational-approach.html on Oct. 29, 2020. "A Rational Approach to Disinfection and Sterilization" "Guideline for Disinfection and Sterilization in Healthcare Facilities (2008)".
De Smet et al. Jan. 2000 *Microbiology (Reading)*. 146(Pt 1):199-208. "Three pathways for trehalose biosynthesis in mycobacteria".

* cited by examiner

*Primary Examiner* — Bin Shen

(57) ABSTRACT

A device for monitoring the effectiveness of a decontamination process, the device including a bacteria cell as the indicator test organism and optionally a substrate, where the indicator test organism may include a *Mycobacteria terrae* cell, and methods of using the monitoring device to evaluate the efficacy of a decontamination process.

9 Claims, 1 Drawing Sheet

DEVICE FOR MONITORING EFFICACY OF A DECONTAMINATION PROCESS COMPRISING A BACTERIA CELL AND METHOD OF USING

CROSS REFERENCE TO RELATED APPLICATIONS

This application claims priority from U.S. Provisional Application Ser. No. 62/609,624, filed Dec. 22, 2017, the disclosure of which is incorporated by reference in its entirety herein.

TECHNICAL FIELD

The present disclosure relates to a device including a bacteria cell for monitoring the efficacy of a medical device reprocessing system and a method for using such monitoring device including a bacteria cell.

BACKGROUND

Healthcare-associated infections are commonly linked to contaminated medical devices, and more healthcare-associated infections are linked to contaminated endoscopes than to any other medical device. A majority of these complex, reusable surgical tools are incompatible with existing sterilization technologies. Minimally, hospitals are required to use high-level disinfection processes to reprocess endoscopes between patients.

One way to monitor medical device reprocessing processes is to use minimum effective concentration strips to test the concentration of a disinfectant prior to running the decontamination cycle. Though it may be useful to know the concentration of disinfectant, these strips provide no information about the effectiveness of bacterial kill during the decontamination cycle.

SUMMARY

In one aspect, provided is a device for monitoring the effectiveness of a decontamination process, the device comprising a bacteria cell. In some embodiments, the device may further comprise a substrate.

In another aspect, provided is a method of detecting the presence of viable microorganisms after a high-level disinfection cycle, the method comprising exposing a bacteria cell to a sterilant in a high-level disinfection cycle, contacting the bacteria cell with a growth medium to provide a culture, and correlating a change in the appearance of the growth medium with presence of viable microorganisms.

Features and advantages of the present disclosure will be further understood upon consideration of the detailed description as well as the appended claims.

Figure 1:
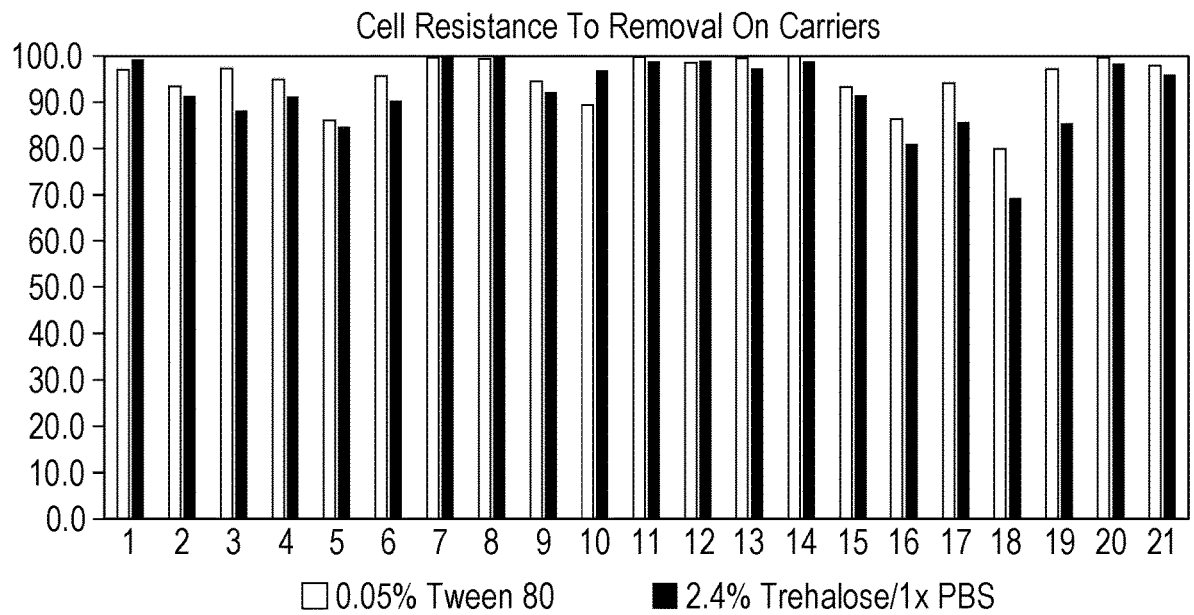
FIG. 1 is a graph of *M. terrae* cell resistance to removal on carriers prepared with different coating solutions.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Devices useful for monitoring the effectiveness of decontamination processes, e.g., sterilization, high-level disinfection, commonly use a highly resistant organism, e.g., a bacterial spore, as the indicator test organism. However, in some decontamination processes, such as, for example, high-level disinfection cycles that employ relatively short exposure times (e.g., five minutes) and low temperatures (e.g., 25-30° C.), bacterial spores may be too resistant to function as an effective indicator organism. Provided herein is a device for monitoring the effectiveness of a decontamination process, the device including a bacteria cell as the indicator test organism.

The terms "decontamination" and "decontamination process" as used herein means a process through which instruments and/or supplies may be cleaned, and refer to both sterilization and high-level disinfection processes.

The terms "sterilant" and "sterilant liquid" as used herein refer to a solution, e.g. peracetic acid ("PAA") solution, ortho-phthalaldehyde ("OPA") solution, glutaraldehyde solution, that may be used in a decontamination process such as, for example, a sterilization process and/or a high-level disinfection process.

In some embodiments, the bacteria cell of the disclosed monitoring device may be a *Mycobacteria* cell. Particularly for high-level disinfection, *Mycobacteria* are considered highly resistant organisms, due in part to their waxy lipid coat that provide resistance to sterilants employed for decontamination kill during a high-level disinfection process. In some embodiments, the *Mycobacteria* cell may be a *Mycobacteria terrae* cell, such as those commercially available as "ATCC 15755" from American Type Culture Collection, Manassas, Md. *Mycobacteria terrae* may be a desirable indicator organism from a safety perspective, as it is generally viewed as a nonpathogenic species of *Mycobacteria*, and would thus not introduce harmful bacteria into a decontamination system.

*Mycobacteria terrae* cells useful in embodiments of the present disclosure may be cultivated by methods known in the art. It was surprisingly discovered that the resistance performance of *Mycobacteria* terrae cells, i.e., resistance to being killed by a sterilant, increased with increased growth time before harvesting. In some embodiments, *Mycobacteria terrae* cells useful in embodiments of the present disclosure may be cultivated for example, on an agar medium or in a liquid medium, for at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 32 days, at least 33 days, at least 34 days, or at least 35 days before harvesting.

In some embodiments, a device of the present disclosure may further include a substrate. The substrate may comprise a material having a particular characteristic, for example, the substrate may comprise a porous material, a non-porous material, a hydrophilic material, a hydrophobic material, and combinations thereof. In some embodiments, the substrate may be selected from the group consisting of a paper, a polymeric material, and combinations thereof. In some embodiments, the paper may include, for example, a cellulosic paper, a silica paper, and combinations thereof. In some embodiments, the polymeric material may include, for example, a polyethylene, a polypropylene, polyurethane, a cellulose, a nylon, a rayon, and combinations thereof.

In some embodiments, the substrate may include a film, a membrane, a woven web (e.g., a cloth), a non-woven web, a metal, a laminate, a glass, and combinations thereof. In some embodiments, the membrane may include a nylon membrane, a cellulose membrane, a polytetrafluoroethylene, membrane, a polyethersulfone membrane, a cellulose acetate membrane, and combinations thereof. In some embodiments, the non-woven web comprises a glass fiber, a polypropylene fiber, a polyester fiber, a rayon fiber, a nylon fiber, a cellulose fiber (e.g., cotton, linen, wood), and combinations thereof. In some embodiments, the nonwoven fabric includes meltblown fibers (e.g., meltblown fibers of a hydrophobic thermoplastic olefin). In some embodiments, the laminate comprises polyethylene terephthalate and paper.

A substrate useful in embodiments of the present disclosure can have any desirable geometry, such as, for example, rectangular, circular, oval, elliptical, trapezoidal, triangular, star, crescent, and combinations thereof. In some embodiments, the substrate may have a surface area of 0.01 $cm^2$-100 $cm^2$, e.g., 0.1 $cm^2$-10 $cm^2$, 0.3 $cm^2$-5 $cm^2$. Desirably, the substrate surface area is sufficient to accommodate a bacteria population of $1 \times 10^6$ CFU/substrate to $1 \times 10^{10}$ CFU/substrate, e.g., $1 \times 10^8$ CFU/substrate, where "CFU" refers to a "colony-forming unit." In some embodiments, the substrate coated with bacteria may be dried, for example, by allowing any solvents in which the bacteria were suspended to evaporate at ambient conditions (about 23° C.) and/or by heating the bacteria-coated substrate in an oven at 40° C. for 30-60 minutes.

A monitoring device of the present disclosure may be readily incorporated into decontamination monitoring systems known in the art such as those described, for example, in PCT/US2017/056250 (Bommarito et al.) and U.S. Patent App. No. 62/592,547 (Bennaars-Eiden et al.), the contents of which are hereby incorporated by reference in their entireties.

In another aspect, provided is a method of detecting the presence of viable microorganisms after the microorganisms have been exposed to a decontamination process. The method includes exposing a bacteria cell to a sterilant in a decontamination cycle, e.g., a high-level disinfection cycle. Sterilants that may be used in embodiments of the present disclosure include, for example, ortho-phthalaldehyde, glutaraldehyde, hydrogen peroxide, peracetic acid, and combinations thereof. In some embodiments, the bacteria cell may be a *Mycobacteria* cell. In some embodiments, the bacteria cell may be a *Mycobacteria terrae* cell. In some embodiments, the bacteria cell may be coated on a substrate, as described above, prior to exposure to the decontamination process.

After completion of the decontamination process, the exposed bacteria cell may be contacted with a growth medium, such as, for example, a liquid, solid, or gel growth medium, to provide a culture, such that a viable cell will be capable of growth. The growth culture including the exposed bacteria may be heated, for example, to 20° C. to 56° C. for up to about 21 days, to facilitate growth of any viable bacteria cells. In the event that a cell is capable of growth after exposure to a decontamination cycle, such growth may be evidenced by, for example, a change in appearance of the growth medium, such as, for example, a change in turbidity, opacity, color, luminescence (e.g., chemiluminescence, fluorescence, bioluminescence), and combinations thereof, i.e., a change in the appearance of the growth medium may be correlated with presence of viable microorganisms and potentially the need for additional decontamination activities. Alternatively, a lack of change in the appearance of the growth medium may be correlated with the absence of viable microorganisms following the decontamination process, providing evidence of a successful decontamination process.

EXAMPLES

Unless otherwise noted, all parts, percentages, ratios, etc. in the Examples and the rest of the specification are by weight.

Materials

TABLE 1

Experimental Materials

| Material | Source |
| --- | --- |
| *Mycobacterium terrae* ATCC 15755 | American Type Culture Collection, Manassas, VA |
| Glycerol #GX0190-6 | MilliporeSigma, Burlington, MA |
| Middlebrook 7H10 agar-solid medium # 262710 | Becton, Dickinson and Company, Franklin Lakes, NJ |
| Middlebrook OADC Enrichment. BBL # 212351 | Becton, Dickinson and Company, Franklin Lakes, NJ |
| Bovine serum albumin ("BSA"); Fraction V; cat. no. 100-021 | Roche Applied Science, Penzberg, Germany |
| Deionized water; deionized, filtered, Milli-Q Gradient System | Millipore, Waltham, MA |
| Phosphate buffered saline ("PBS") 10X concentrate, # P5493-1L | Sigma-Aldrich, St. Louis, MO |
| PET/Paper Laminate | 3M, Saint Paul, MN |
| 1292E barrier web | 3M, Saint Paul, MN |
| Mask Tie String 1292E | 3M, Saint Paul, MN, |
| 1294 barrier Web | 3M, Saint Paul, MN |
| Sontara 8005 Coated with GPEI (25% guanylated) | Dupont, Wilmington, DE |
| Animal derived decaglyn 1292 barrier web | 3M, Saint Paul, MN |
| Tesin SP 1200 silica paper | PPG Industries, Monroeville, PA |
| PET film plasma treated | 3M, Saint Paul, MN |
| 8005 PET | Dupont, Wilmington, DE |
| 100% Cellulose paper | 3M, Saint Paul, MN |

TABLE 1-continued

Experimental Materials

| Material | Source |
| --- | --- |
| Cellulose Acetate membrane | Millipore, Waltham, MA |
| Durapore PES 8F | Millipore, Waltham, MA |
| 0.8 μm Nylon membrane 08 zn | Millipore, Waltham, MA |
| Magma membrane | 3M, Saint Paul, MN |
| Cellulose | Millipore, Waltham, MA |
| 65 gsm 9d PP fibers | 3M, Saint Paul, MN |
| SRBI polypropylene Tub | 3M, Saint Paul, MN |
| Polypropylene Loops | 3M, Saint Paul, MN |
| Polypropylene 9d PP (PET film backing) | 3M, Saint Paul, MN |
| Polymer sheet number 10 | 3M, Saint Paul, MN |
| Polymer sheet number 11 | 3M, Saint Paul, MN |
| Horse serum, # H0146-10ML | Sigma-Aldrich, St. Louis, MO |
| Sodium thiosulfate, #72049 | Sigma-Aldrich, St. Louis, MO |
| Tween 80, # 103170 | MP Biomedicals, LLC |
| Lecithin, Letheen broth # BP0245500 | 3M, St. Paul, MN |
| RAPICIDE ortho-phthalaldehyde ("OPA") # ML02-0127 | Medivators, Plymouth, MN |
| RAPICIDE peracetic acid ("PAA") reagents A and B, # ML02-0117 | Medivators, Plymouth, MN |
| Automated endoscope reprocessor ("AER") DSD 201 | Medivators, Plymouth, MN |
| Butterfield's buffer (pH 7.2 ± 0.2, monobasic potassium phosphate buffer solution), #83008-093 | VWR, West Chester, PA |

Methods

The growth media and solutions were prepared as follows:

Middlebrook 7H10 Agar Solid Medium Containing 10% Oleic Acid Albumin Dextrose Catalase ("OADC") Enrichment and 0.5% Glycerol Dissolve 19 g Middlebrook 7H10 powder in 900 ml deionized water and autoclave 20 minutes at 121° C. Cool for 30 min with stirring and add 100 ml Middlebrook OADC Enrichment solution aseptically to cooled media. Add 10 ml of 50% (w/v) glycerol aseptically to cooled media. The cooled media was added to sterile plates and allowed to solidify.

For 7H10 powder, the approximate amounts of the components per 900 ml are: 0.5 g ammonium sulfate, 1.5 g monopotassium phosphate, 1.5 g disodium phosphate, 0.4 g sodium citrate, 25.0 mg magnesium sulfate, 0.5 g calcium chloride, 1.0 mg zinc sulfate, 1.0 mg copper sulfate, 0.5 g L-glutamic acid (sodium salt), 0.04 μg malachite green, and 15 g Agar.

Tween 80, 20% (v/v)

Add 20 ml Tween 80 (MP Biomedicals, LLC, catalogue #103170) to 80 ml deionized water. If needed, heat Tween solution to 56° C. to speed solubilization of Tween 80. Sterilize by filtration through 0.22-μm membrane. Store up to 2 months at room temperature. The final concentration of Tween 80 used in the media in this unit is 0.05% (v/v).

1×PBST, Tween 80, 0.01% (w/v)

Weigh out 0.1 g Tween 80. Add 100 ml of 10×PBS. Add 900 ml deionized water. If needed, heat to 56° C. to speed solubilization of Tween 80. Sterilize by filtration through 0.22-μm membrane. Store up to 2 month at room temperature. The final concentration of Tween 80 used in the media in this unit is 0.05% (v/v).

Ortho-Phthalaldehyde ("OPA")

OPA Solution Preparation:

RAPICIDE OPA: Dilute titrated 0.55 wt % RAPICIDE OPA to a concentration of 0.35 wt % with deionized water. To make 1 L of a 0.35 wt % RAPICIDE OPA solution, weigh out 636.36 g of 0.55 wt % OPA and weigh out 363.64 g of deionized water. Mix thoroughly before use. Place solution in 25° C. water bath to equilibrate for at least 10 minutes before use.

Glycine Neutralizing Solution Preparation:

Mix Horse serum with 0.07% Lecithin, 1% glycine and 0.5% Tween 80. Filter sterilize the solution with 0.2 micron filter unit. Place solution in 25° C. water bath to equilibrate for at least 10 minutes before use.

Peracetic Acid ("PAA")

PAA Solution Preparation:

Into a 50 ml polypropylene tube, pipet 0.85 ml of RAPICIDE Part A, 0.85 ml of RAPICIDE part B, and mix with 48.3 ml of distilled water. Vortex to mix thoroughly. Place tube in 30° C. water bath to equilibrate for at least 10 minutes before use.

Thiosulfate Neutralizing Solution Preparation:

Neutralizer (1% sodium thiosulfate with 0.05% Tween 80): Weigh out 0.5 g of sodium thiosulfate and dissolve in 50 ml of 0.05% Tween 80. Vortex to mix thoroughly. Place solution in 30° C. water bath to equilibrate for at least 10 minutes before use.

Coating of Carriers with Mycobacteria terrae

M. terrae cells were inoculated and incubated for 14-days and 21-days at 37° C. on Middlebrook 7H9 agar plates containing 10% oleic acid albumin dextrose catalase enrichment ("OADC") and 0.5% of glycerol prepared as described above. The bacterial cells were harvested by scraping the agar surface. The harvested cells were resuspended in either 0.05% Tween 80 or 2.4% Trehalose/1×PBS. The cell population was determined by serial dilution and plating. The cells were adjusted to a concentration of $1\times10^8$ cfu/mL prior to coating. For comparison purposes, all the carriers were cut to the same diameter size of 0.25 inch using a Mayhew Pro hollow punch (Mayhew Steel Products, Inc., Turners Falls, Mass.). Ten microliters of cell suspension was pipetted and deposited on individual carrier discs of different materials (see Table 4) with a target population of $1\times10^8$ CFU/carrier. The coated carriers were dried at room temperature for 16-24 hours in a Forma 1400 series ventilated biosafety cabinet (Thermo Fisher Scientific Inc., Coon Rapids, Minn.).

Ten carrier discs for each type of material were submerged in a 50 ml Falcon tube containing 10 mL of 1×PBS buffer, pH 7.4 and vortexed for 10 seconds at a maximum speed. 100 μl of supernatant was pipetted and plated on Middlebrook 7H9 agar plates for population recovery in order to assess adhesion of the cells to the carrier material. Assessment of *M. terrae* Cells Resistance to High-Level Disinfection ("HLD")

Cell Suspension Testing

OPA Time course: Exposure to OPA for various contact time points at 25° C. at the minimum effective concentration of RAPICIDE OPA (0.35 wt %). 10 μl of *M. terrae* cell samples at a target concentration of at least 1×10$^8$ cfu/mL were added to a 1.5 mL Eppendorf tube containing 400 μL of 0.35 wt % OPA for the appropriate contact time (30 seconds to 3 minutes) in a 25° C. water bath. At the end of each contact time, samples were neutralized by adding with 600 μL of glycine neutralizing solution (described above) for 15 minutes at 25° C. Samples were centrifuged for 10 minutes at 14000 rpm at 4° C. The supernatant was decanted off and the bacterial cells were resuspended in 1 mL of PBST buffer. Serial dilutions 1:10 were made of each sample and 1 mL of each dilution was plated on Middlebrook 7H10 agar with OADC enrichment. Plates were incubated at 37° C. for 14-21 days.

PAA Time course: Exposure to PAA for various contact time points at 30° C. at the minimum effective concentration of RAPICIDE PAA (850 ppm). 10 μl of *M. terrae* cell samples at a target concentration of at least 1×10$^8$ cfu/mL were added to a 1.5 mL Eppendorf tube containing 400 μL of 850 ppm PAA for the appropriate contact time ranging from 30 seconds to 5 minutes using duplicate samples for each sample in a 30° C. water bath. At the end of each contact time, samples were neutralized by adding 600 μL of 3% sodium thiosulfate with 0.05% Tween 80 for 15 mins at 30° C. Samples were centrifuged for 10 mins at 14000 rpm at 4 C. The supernatant was decanted off and samples were resuspended in 1 ml of BBL buffer. Serial dilutions (1:10) were made of each sample and 1 mL of each dilution was plated on Middlebrook 7H10 agar with Middlebrook OADC enrichment. Plates were incubated at 37° C. for 14-21 days.

Example 1

*Mycobacterium terrae* Cell Resistance Orto-Phthalaldehyde ("OPA")

Impact of Cell Culture Duration on Bacteria Resistance to the OPA.

*M. terrae* cells were inoculated and incubated for 14 and 21 days at 37° C. on Middlebrook 7H9 agar plates containing 10% oleic acid albumin dextrose catalase enrichment ("OADC") and 0.5% of glycerol. The bacterial cells were harvested and OPA (high-level disinfectant) was applied at different time points (0 minutes; 30 seconds; and 3 minutes). The resistance was tested as described above and the performance data was collected and plotted.

The *M. terrae* cells harvested at 14 and 21 days incubation for growth were exposed to the OPA for 30 seconds (survival cycle) and 3 minutes (kill cycle). A control with cells not exposed to the OPA was also tested. The population of the cells harvested at day 7 was too low to allow for testing of these cells using a target population of 1×10$^8$ cfu/mL. Results are shown in Tables 2 and 3.

14 Days Growth Culture

As the data in Table 2 show, the results from 14 days growth may be classified into two groups: 1) three to four log reduction for cells exposed to OPA for 30 seconds, and 2) six log reduction when cells are exposed to OPA for 3 minutes.

The recommendation of the Food and Drug Administration (FDA) is 6 log reduction for a kill cycle and 0 log reduction for a survival cycle. The data show that *M. terrae* cells responded to the OPA treatment. The OPA treatment for 30 seconds could be considered as a fractional cycle since it showed a log reduction between 0 and 6. The 3-minute exposure was a kill cycle (i.e., 6 log reduction).

TABLE 2

*M. terrae* Cells performance against OPA after 14 Days Growth Culture

| Exposure time (minutes) | Sample | Log recovered population (cfu) | Log reduction |
|---|---|---|---|
| 0 | Replicate 1 | 6.68 | 0.00 |
| 0.5 | Replicate 1 | 3.11 ± 0.54 | 3.57 |
|  | Replicate 2 | 3.05 ± 0.69 | 3.63 |
| 3 | Replicate 1 | 0.00 ± 0.00 | 6.68 |
|  | Replicate 2 | 0.00 ± 0.00 | 6.68 |

21 Days Growth Culture

Data presented in Table 3 show that 21-days growth exhibited two groups of data: 1) about one log reduction for cells exposed to OPA for 30 seconds, and 2) six log reduction for cells exposed to OPA for 3 min with 6 log reduction. The OPA treatment for 30 seconds could be considered as a survival cycle since it showed no log reduction. *M. terrae* cells exposure to OPA for 3 minutes showed a kill cycle (i.e., 6 log reduction).

TABLE 3

*M. terrae* Cells Performance against OPA after 21 days Growth Culture

| Exposure time (minutes) | Sample | Log recovered population (cfu) | Log reduction |
|---|---|---|---|
| 0 | Replicate 1 | 6.98 | 0.00 |
| 0.5 | Replicate 1 | 6.19 ± 0.26 | 0.79 |
|  | Replicate 2 | 6.1 ± 0.39 | 0.88 |
| 3 | Replicate 1 | 0.83 ± 0.67 | 6.15 |
|  | Replicate 2 | 0.28 ± 0.47 | 6.70 |

Resistance performance of cells after 14-days growth compared against 21-days growth surprisingly showed that the resistance to the OPA increases with the age of the culture. This is illustrated by higher log reduction for 14-days growth compared to 21-days growth when cells were exposed for 30 seconds to the OPA solution.

Example 2

Carrier Screening, *Mycobacterium terrae* Cell Coating, and Testing

Twenty-one different types of carriers including paper, nonwovens, and films were screened and tested according to the protocol described above. The experiments were replicated twice. Carrier performance for cells suspended in both 0.05% Tween 80 and 2.4% trehalose/1×PBS are presented respectively in Tables 4 and 5. The resistance performance to cell removal was tested by subtracting the number of cells removed, during vortexing, from the population initially coated.

TABLE 4

Carrier Performance for Cells Suspended in 0.05% Tween 80

| Carrier Name | Carrier Number | Replicate 1 | Replicate 2 | Average | Coated population | Detached cell population | Residual cell population | Resistance to removal (%) |
|---|---|---|---|---|---|---|---|---|
| PET/Paper Laminate | 1 | 38 | 24 | 31 | 1.E+08 | 3.E+06 | 9.69E+07 | 96.9 |
| 1292E barrier web | 2 | 66 | 66 | 66 | 1.E+08 | 7.E+06 | 9.34E+07 | 93.4 |
| Mask Tie String 1292E | 3 | 31 | 24 | 27.5 | 1.E+08 | 3.E+06 | 9.73E+07 | 97.3 |
| 1294 barrier Web | 4 | 53 | 50 | 51.5 | 1.E+08 | 5.E+06 | 9.49E+07 | 94.9 |
| Sontara 8005 Coated with GPEI (25% guanylated) | 5 | 120 | 158 | 139 | 1.E+08 | 1.E+07 | 8.61E+07 | 86.1 |
| Animal derived decaglyn 1292 barrier web | 6 | 41 | 47 | 44 | 1.E+08 | 4.E+06 | 9.56E+07 | 95.6 |
| Tesin SP 1200 silica paper | 7 | 8 | 1 | 4.5 | 1.E+08 | 5.E+05 | 9.96E+07 | 99.6 |
| PET film plasma treated | 8 | 9 | 6 | 7.5 | 1.E+08 | 8.E+05 | 9.93E+07 | 99.3 |
| 8005 PET | 9 | 54 | 57 | 55.5 | 1.E+08 | 6.E+06 | 9.45E+07 | 94.5 |
| 100% Cellulose paper | 10 | 105 | 108 | 106.5 | 1.E+08 | 1.E+07 | 8.94E+07 | 89.4 |
| Cellulose Acetate membrane | 11 | 2 | 4 | 3 | 1.E+08 | 3.E+05 | 9.97E+07 | 99.7 |
| Durapore PES 8F | 12 | 20 | 10 | 15 | 1.E+08 | 2.E+06 | 9.85E+07 | 98.5 |
| 0.8 µm Nylon membrane 08 zn | 13 | 6 | 6 | 6 | 1.E+08 | 6.E+05 | 9.94E+07 | 99.4 |
| Magma membrane (3M purification) | 14 | 1 | 2 | 1.5 | 1.E+08 | 2.E+05 | 9.99E+07 | 99.9 |
| Cellulose | 15 | 60 | 74 | 67 | 1.E+08 | 7.E+06 | 9.33E+07 | 93.3 |
| 65 gsm 9d PP fibers | 16 | 130 | 144 | 137 | 1.E+08 | 1.E+07 | 8.63E+07 | 86.3 |
| SRBI polypropylene Tub | 17 | 42 | 77 | 59.5 | 1.E+08 | 6.E+06 | 9.41E+07 | 94.1 |
| Polypropylene Loops | 18 | 171 | 231 | 201 | 1.E+08 | 2.E+07 | 7.99E+07 | 79.9 |
| Polypropylene 9d PP (PET film backing) | 19 | 34 | 26 | 30 | 1.E+08 | 3.E+06 | 9.70E+07 | 97.0 |
| Polymer sheet number 10 | 20 | 5 | 3 | 4 | 1.E+08 | 4.E+05 | 9.96E+07 | 99.6 |
| Polymer sheet number 11 | 21 | 23 | 20 | 21.5 | 1.E+08 | 2.E+06 | 9.79E+07 | 97.9 |

TABLE 5

Carrier Performance for Cells Suspended in 2.4% Trehalose/1x PBS

| Carrier Name | Carrier Number | Replicate 1 | Replicate 2 | Average | Coated population | Detached cell population | Residual cell population | Resistance to removal (%) |
|---|---|---|---|---|---|---|---|---|
| PET/Paper Laminate | 1 | 9 | 7 | 8 | 1.E+08 | 8.E+05 | 9.92E+07 | 99.2 |
| 1292E barrier web | 2 | 101 | 74 | 87.5 | 1.E+08 | 9.E+06 | 9.13E+07 | 91.3 |
| Mask Tie String 1292E | 3 | 127 | 109 | 118 | 1.E+08 | 1.E+07 | 8.82E+07 | 88.2 |
| 1294 barrier Web | 4 | 79 | 99 | 89 | 1.E+08 | 9.E+06 | 9.11E+07 | 91.1 |

TABLE 5-continued

Carrier Performance for Cells Suspended in 2.4% Trehalose/1x PBS

| Carrier Name | Carrier Number | Replicate 1 | Replicate 2 | Average | Coated population | Detached cell population | Residual cell population | Resistance to removal (%) |
|---|---|---|---|---|---|---|---|---|
| Sontara 8005 Coated with GPEI (25% guanylated) | 5 | 147 | 161 | 154 | 1.E+08 | 2.E+07 | 8.46E+07 | 84.6 |
| Animal derived decaglyn 1292 barrier web | 6 | 97 | 98 | 97.5 | 1.E+08 | 1.E+07 | 9.03E+07 | 90.3 |
| Tesin SP 1200 silica paper | 7 | 1 | 5 | 3 | 1.E+08 | 3.E+05 | 9.97E+07 | 99.7 |
| PET film plasma treated | 8 | 4 | 3 | 3.5 | 1.E+08 | 4.E+05 | 9.97E+07 | 99.7 |
| 8005 PET | 9 | 59 | 99 | 79 | 1.E+08 | 8.E+06 | 9.21E+07 | 92.1 |
| 100% Cellulose paper | 10 | 40 | 24 | 32 | 1.E+08 | 3.E+06 | 9.68E+07 | 96.8 |
| Cellulose Acetate membrane | 11 | 6 | 18 | 12 | 1.E+08 | 1.E+06 | 9.88E+07 | 98.8 |
| Durapore PES 8F | 12 | 11 | 10 | 10.5 | 1.E+08 | 1.E+06 | 9.90E+07 | 99.0 |
| 0.8 μm Nylon membrane 08 zn | 13 | 25 | 30 | 27.5 | 1.E+08 | 3.E+06 | 9.73E+07 | 97.3 |
| Magma membrane (3M purification) | 14 | 8 | 16 | 12 | 1.E+08 | 1.E+06 | 9.88E+07 | 98.8 |
| Cellulose | 15 | 104 | 66 | 85 | 1.E+08 | 9.E+06 | 9.15E+07 | 91.5 |
| 65 gsm 9d PP fibers | 16 | 151 | 229 | 190 | 1.E+08 | 2.E+07 | 8.10E+07 | 81.0 |
| SRBI polypropylene Tub | 17 | 144 | 142 | 143 | 1.E+08 | 1.E+07 | 8.57E+07 | 85.7 |
| Polypropylene Loops | 18 | 310 | 304 | 307 | 1.E+08 | 3.E+07 | 6.93E+07 | 69.3 |
| Polypropylene 9d PP (PET film backing) | 19 | 80 | 211 | 145.5 | 1.E+08 | 1.E+07 | 8.55E+07 | 85.5 |
| Polymer sheet number 10 | 20 | 31 | 4 | 17.5 | 1.E+08 | 2.E+06 | 9.83E+07 | 98.3 |
| Polymer sheet number 11 | 21 | 48 | 35 | 41.5 | 1.E+08 | 4.E+06 | 9.59E+07 | 95.9 |

A plot of *M. terrae* cell resistance performance to removal from a coated carrier as a function of type of carrier in two different buffers is shown in FIG. 1. Referring to FIG. 1, cells resuspended in 0.05% Tween 80 presented overall somewhat higher resistance to removal compared to cells resuspended in 2.4% Trehalose/1×PBS.

Example 3

*Mycobacterium terrae* Cell Resistance to Peracetic Acid ("PAA")

Figure 2:
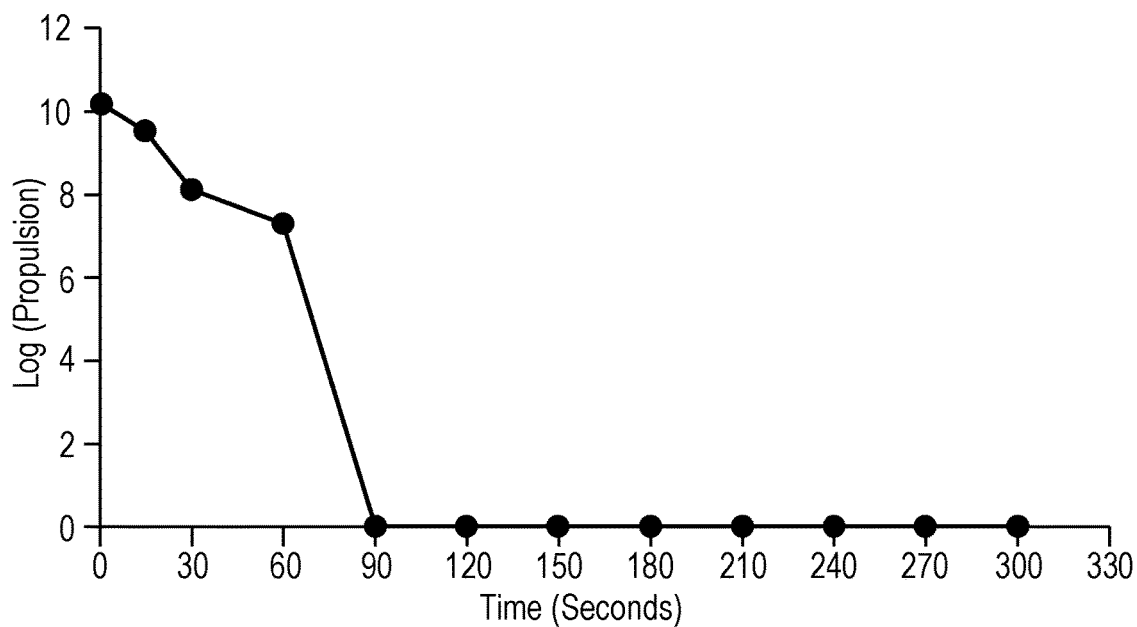
FIG. 2 is a graph of *M. terrae* cells performance against PAA after 21 days growth culture.

The procedure of Example 1 was repeated using 21-days growth cells, with the *M. terrae* cells exposed to PAA instead of OPA. Data presented in Table 6 and FIG. 2 show a 6 log reduction in *M. terrae* cells after about 75 seconds exposure to PAA at 30° C., suggesting that *M. terrae* can be used to monitor endoscope reprocessing with PAA as a high-level disinfectant.

TABLE 6

*M. terrae* cells performance against PAA after 21 days growth culture

| Exposure time (seconds) | *M. terrae* Population (CFU) | Log Population | Log reduction |
|---|---|---|---|
| 1 | 1.53E+10 | 10.2 | 0.0 |
| 15 | 3.45E+09 | 9.5 | 0.7 |
| 30 | 1.40E+08 | 8.1 | 2.1 |
| 60 | 2.00E+07 | 7.3 | 2.9 |
| 90 | 1.00E+00 | 0 | 10.2 |
| 120 | 1.00E+00 | 0 | 10.2 |
| 150 | 1.00E+00 | 0 | 10.2 |
| 180 | 1.00E+00 | 0 | 10.2 |
| 210 | 1.00E+00 | 0 | 10.2 |
| 240 | 1.00E+00 | 0 | 10.2 |
| 270 | 1.00E+00 | 0 | 10.2 |
| 300 | 1.00E+00 | 0 | 10.2 |

Examples 1-3 demonstrate that *Mycobacterium terrae* can be used as a predicate to monitor endoscope reprocessing with high-level disinfectant, such as, for example, OPA and PAA, as well as sterilization of surgical instruments. These resistant microbial cells can be tested in suspension form or immobilized by coating on different carriers, such as films and nonwoven materials and used as independent biological indicators.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A device for monitoring the effectiveness of a decontamination process, the device comprising:
    a substrate; and
    a dry coating disposed thereon;
        wherein the coating comprises a plurality of bacterial cells of the *Mycobacterium* genus;
        wherein the plurality of bacterial cells are *Mycobacteria terrae* cells;
        wherein the coating comprises at least $1 \times 10^6$ CFU of the bacteria;
        wherein the dry coating further comprises polyoxyethylene sorbitan monooleate.

2. The device of claim 1, wherein the substrate comprises at least one of a paper, a polymeric material, a film, a membrane, a woven web, a non-woven web, a metal, a laminate, a glass, or combinations thereof.

3. The device of claim 2, wherein the paper comprises at least one of a cellulosic paper, a silica paper, or combinations thereof.

4. The device of claim 2, wherein the film comprises a polymeric material.

5. The device of claim 4, wherein the polymeric material is selected from the group consisting of a polyethylene, a polypropylene, polyurethane, a cellulose, a nylon, a rayon, and combinations thereof.

6. The device of claim 2, wherein the membrane comprises at least one of a nylon membrane, a cellulose membrane, a polytetrafluoroethylene membrane, a polyethersulfone membrane, a cellulose acetate membrane, or combinations thereof.

7. The device of claim 2, wherein the non-woven web comprises at least one of a glass fiber, a polypropylene fiber, a polyester fiber, a cellulose fiber, or combinations thereof.

8. The device of claim 2, wherein the laminate comprises polyethylene terephthalate and paper.

9. The device of claim 1, wherein the plurality of bacterial cells are viable bacterial cells.

* * * * *